United States Patent
Corey

(10) Patent No.: US 10,822,310 B2
(45) Date of Patent: Nov. 3, 2020

(54) PREVENTION AND TREATMENT OF HUMAN METABOLIC SYNDROME INCLUDING TYPE 2 DIABETES, STEATOHEPITITIS AND RELATED CONDITIONS USING NON-ABSORBABLE, ORALLY ADMINISTERED COMPOUNDS

(71) Applicant: Elias James Corey, Cambridge, MA (US)

(72) Inventor: Elias James Corey, Cambridge, MA (US)

( * ) Notice: Subject to any disclaimer, the term of this patent is extended or adjusted under 35 U.S.C. 154(b) by 73 days.

(21) Appl. No.: 16/341,523

(22) PCT Filed: Nov. 20, 2018

(86) PCT No.: PCT/US2018/062106
§ 371 (c)(1),
(2) Date: Apr. 12, 2019

(87) PCT Pub. No.: WO2019/118141
PCT Pub. Date: Jun. 20, 2019

(65) Prior Publication Data
US 2019/0300489 A1    Oct. 3, 2019

Related U.S. Application Data

(60) Provisional application No. 62/598,744, filed on Dec. 14, 2017.

(51) Int. Cl.
| | |
|---|---|
| *C07D 235/14* | (2006.01) |
| *A61K 9/00* | (2006.01) |
| *A61K 31/4184* | (2006.01) |
| *A61P 1/16* | (2006.01) |
| *A61P 3/00* | (2006.01) |

(52) U.S. Cl.
CPC .......... *C07D 235/14* (2013.01); *A61K 9/0053* (2013.01); *A61K 31/4184* (2013.01); *A61P 1/16* (2018.01); *A61P 3/00* (2018.01)

(58) Field of Classification Search
CPC ..... A61K 31/4184; A61K 9/0053; A61P 1/16; A61P 3/00; C07D 235/14
See application file for complete search history.

(56) References Cited

U.S. PATENT DOCUMENTS

| | | |
|---|---|---|
| 3,935,314 A | 1/1976 | Watts |
| 4,329,417 A | 5/1982 | Nagatini et al. |
| 4,487,936 A | 12/1984 | Szoke et al. |
| 6,640,401 B2 | 11/2003 | Chen et al. |
| 2008/0249030 A1 | 10/2008 | Potier |
| 2017/0239196 A1 | 8/2017 | Brady et al. |

OTHER PUBLICATIONS

2005, Pubchem-CID: 145820 Create Date: Mar. 26, 2005 (Mar. 26, 2005) pp. 1-19; p. 3.
2005, Pubchem-CID: 693231 Create Date: Jul. 7, 2005 (Jul. 7, 2005) pp. 1-14; p. 4, Fig.
2010, Zagol-Ikapitte et al. 'Characterization of scavengers of gamma-ketoaldehydes that do not inhibit prostaglandin biosynthesis', Chern Res Toxicol., 2010, vol. 23(1), pp. 240-250. doi:10.1021/tx900407a; abstract; p. 8, para 2; p. 10, para 2; p. 21, Scheme 1; p. 23, Table 1.
International Search Report issued for PCT/US2018/62106.
Written Opinion issued for PCT/US2018/62106.

*Primary Examiner* — Savitha M Rao
(74) *Attorney, Agent, or Firm* — Neifeld IP Law, PLLC

(57) ABSTRACT

Compounds and oral pharmaceutical compositions which neutralize microbially-produced electrophilic carbonyl species, comprising:
a non-absorbable compound containing one or more nitrogen nucleophiles having a first pKa between 5 and 10, and a molecular weight less than 800,
wherein said non-absorbable compound reacts locally in the gastrointestinal tract and combines with microbially-produced electrophilic carbonyl species by C—N bond formation, thereby protecting gastrointestinal peptide hormones containing arginine or lysine residues, and also preventing diffusion of said electrophilic species into systemic circulation where they may cause damage to proteins, DNA or RNA that adversely affects health; and a pharmaceutically acceptable carrier or excipient.

6 Claims, No Drawings

PREVENTION AND TREATMENT OF HUMAN METABOLIC SYNDROME INCLUDING TYPE 2 DIABETES, STEATOHEPITITIS AND RELATED CONDITIONS USING NON-ABSORBABLE, ORALLY ADMINISTERED COMPOUNDS

CROSS REFERENCE TO RELATED APPLICATIONS

This application is a 371 National Stage Entry of PCT/US18/62106 filed Nov. 20, 2018, and PCT/US18/62106 claims priority to U.S. Application No. 62/598,744, filed Dec. 14, 2017. The contents of U.S. Application No. 62/598,744, filed Dec. 14, 2017 are incorporated by reference in its entirety.

TECHNICAL FIELD

Pharmaceuticals to regulate metabolism.

BACKGROUND OF THE INVENTION

Diseases such as type 2 diabetes (T2D) and non-alcoholic steatohepatitis (NASH), subsets of a broader condition called metabolic syndrome, constitute a major health problem throughout the world. Better treatments are needed because of their high and increasing incidence and the limitations of existing treatments. The salient hallmark of T2 D, elevated levels of plasma glucose even under fasting conditions leads to serious consequences, including lipid abnormalities, metabolic dysfunction, obesity, hypertension, vascular and heart disease, stroke, neuropathy, nephropathy, retinopathy, pancreatic beta-cell death and other conditions. Individuals with metabolic syndrome are likely to be at elevated risk of brain disorders such as Alzheimer's and Parkinson's disease. Untreated T2D leads to rapid disease progression, increasing insensitivity to insulin, loss of pancreatic insulin synthesis and release, accelerated physical decline, and death.

Current treatments for T2D include: (1) dietary restriction and weight loss; (2) exercise; (3) sulfonyl ureas (which act to stimulate pancreatic beta cell insulin release); (4) metformin—commonly considered to be an activator of AMP-activated protein kinase (AMPK)—see Cell Metabolism, 20, 953-956 (2014); (5) glitazones, e.g. pioglitazone; (6) dipeptidyl peptidase inhibitors, e.g., sitagliptin, which inhibit the breakdown of the natural metabolic regulator GLP-1—see, J. Med. Chem., 48, 141-151 (2005); (7) intravenous GLP-1 (glucagon-like peptide-1),—see Nat. Rev. Endocrinol., 8, 728-742 (2012); (8) intravenous GLP-1 analogs of longer lifetime such as semaglutide and exenatide—see J. Med. Chem., 58, 7370-7380 (2015); and (9) SGLT2 inhibitors such as dapagliflozen and ertugaflozin—see J. Med. Chem., 54, 2952-2960 (2011) and also J. Med. Chem. 51, 1145-1149 (2008), which promote the urinary secretion of glucose and thus reduce blood glucose levels. Despite the availability of these antidiabetic agents there is a need for more effective treatments that prevent, better manage, reverse or cure T2D.

Bariatric surgery has been shown to be a helpful interventional treatment for obesity and metabolic syndrome in individuals with a body mass index of over 35—see New England J. Med., 361, 520-521 (2009). In addition to the principal beneficial effect of weight loss, improved glycemic control can result. However, bariatric surgery carries a substantial risk of harmful complications (ca. 20%). It has been speculated that the benefits of bariatric surgery result from reduction in capacity of the stomach, changes in gastrointestinal hormones or alteration of the microbial flora in the gut. Numerous research studies have linked human gut microbes to metabolic health and T2D—see Nature, 535, 376-381 (2016); Cell Mol. Gasterol. Hepatol., 4, 205-221 (2017); Diabetes Care, 33, 2277-2293 (2010); Endocr. Connect. 5, 1-9 (2016); Science, 352, 586-589 (2016); Nature, 490, 55-60 (2016). There are thousands of types of bacteria in the intestines, thousands of individual bacteria in each ml. of fluid in the gut, and trillions in total. As a result of this complexity, the understanding of the connection between gut microbiorta and T2D is very rudimentary. In contrast, it has long been known that specific bacterial pathogens can produce harmful toxins in the gut that cause a range of illnesses.

SUMMARY OF THE INVENTION

The present invention relates to the prevention and treatment of human metabolic syndrome and related diseases, including type 2 diabetes, non-alcoholic steatohepatitis and various degenerative conditions, using non-absorbable, low-molecular weight, orally administered compounds whose action is restricted to the gut. The discovery of the utility of these compounds depended on the identification of previously unrecognized molecular mechanisms by which normal microbial metabolites produced in the gut can adversely affect the entire body with profound consequences for health. As a result of the elucidation of this mode of action, new orally administered, non-absorbable anti-electrophilic substances were designed that were shown to be remarkably effective in normalizing fasting blood glucose levels in vivo. These discoveries are especially significant because the high degree of safety expected for a therapeutic agent acting only locally in the gut suggests the possibility of widespread use in preventative medicine, in tandem with exercise and weight control, to forestall diabetes, metabolic syndrome, non-alcoholic steatohepatitis and various degenerative conditions including, for example, Parkinson's disease. This invention is also directed to pharmaceutical compositions comprising these anti-electrophilic compounds and their use for any conditions that result from the stochastic production in the intestines of harmful microbial metabolites and release into the general circulation.

An object of the invention is to provide compounds and oral pharmaceutical compositions which neutralize microbially-produced electrophilic carbonyl species, comprising:

a non-absorbable compound containing a sulfonate group and one or more nitrogen nucleophiles having a first pKa between 5 and 10, and a molecular weight less than 800, wherein said non-absorbable compound reacts locally in the gastrointestinal tract and combines with microbially-produced electrophilic carbonyl species by C—N bond formation, thereby protecting gastrointestinal peptide hormones containing arginine or lysine residues, and preventing diffusion of said electrophilic species into systemic circulation where they may cause damage to proteins, DNA or RNA; and a pharmaceutically acceptable carrier or excipient.

Another object of the invention is to provide compounds and pharmaceutical compositions comprising

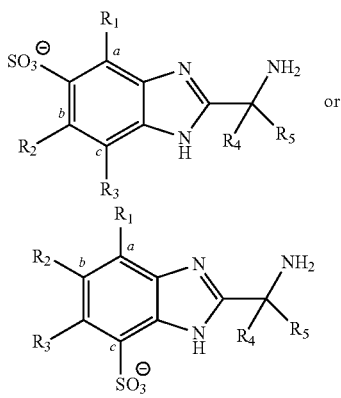

wherein $R_1$, $R_2$, and $R_3$ are independently selected from hydrogen, CN, $C_{1-10}$ alkyl which is linear or branched and which is unsubstituted or substituted with 1-5 halogens or phenyl, which phenyl is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; phenyl which is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; and a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$ alkyl, and $OC_{1-6}$ alkyl, wherein the $C_{1-6}$ alkyl and $OC_{1-6}$ alkyl are linear or branched and optionally substituted with 1-5 halogens;

$R_4$ and $R_5$ are independently selected from H, linear or branched $C_1$-$C_8$-alkyl, aryl or heteroaryl, $R^6$ are independently selected from H, linear or branched $C_{1-8}$ alkyl, aryl or heteroaryl, a molecular weight <800, and a pKa between 5 and 10;

a pharmaceutically acceptable salt, pharmaceutically acceptable N-protected derivative, or individual stereoisomer thereof.

Another object of the invention is to provide a method for protecting gastrointestinal peptide hormones, comprising:

administering an effective amount of an oral pharmaceutical composition that neutralizes microbially-produced electrophilic carbonyl species, which includes a non-absorbable compound containing one or more nitrogen nucleophiles having a first pKa between 5 and 10, and a molecular weight less than 800, wherein said non-absorbable compound reacts locally in the gastrointestinal tract and combines with microbially-produced electrophilic carbonyl species by C—N bond formation, thereby protecting gastrointestinal peptide hormones containing arginine or lysine residues, and preventing diffusion of said electrophilic species into systemic circulation where they may cause damage to proteins, DNA or RNA; and a pharmaceutically acceptable carrier or excipient.

Another object of the invention is to provide a method for suppression of appetite, prevention of weight gain, weight control or obesity.

Another object of the invention is to provide a method for prevention or treatment of human metabolic syndrome, type 2 diabetes, or steatohepatitis.

Another object of the invention is to provide other classes of compounds of low molecular weight, non-absorbable, sulfonate-containing nitrogen nucleophiles (MW<800, pKa between 5 and 10), which can serve as therapeutic agents, acting locally in the intestines to combine (via C—N bond formation) with and neutralize microbially-produced electrophilic carbonyl species. These other classes of compounds include the imidazoles, heteroaromatic 1,2-diamines, azabenzamidines, guanidines, and acyclic diamines described herein.

DETAILED DESCRIPTION OF THE PREFERRED EMBODIMENTS

Two key ideas motivated this discovery. First, normal gut bacterial metabolic products might be capable of reacting with and damaging intestinal hormones which play an essential role in metabolic regulation and human health. Second, the production of such molecular species is linked to food intake and microbial population, but is not under physiological regulation, and therefore, stochastic. Such adverse effects stand in contrast to the beneficial, even essential, role of gut microbes in the conversion of ingested food into molecules that are essential nutrients.

Among the critically important enteroendocrine hormones produced by intestinal cells are the following: (1) Glucagon-like peptide-1 (GLP-1), a member of the incretin family and a potent anti-hyperglycemic hormone which also stimulates insulin production in pancreatic beta cells via interaction with glucokinase; the therapeutic use of GLP-1 for T2D has been mentioned above; (2) Oxyntomodulin, a 37-amino acid peptide hormone which has broad activity in weight and glucose control and also metabolic energy generation—see Molecular Metabolism, 3, 241-251 (2013); (3) Neuropeptide PYY, a 36-amino acid peptide that has multiple ropes including regulation of appetite and pancreatic function—see Cell Reports, 15, 944-950 (2016); Diabetologia, 57, 1763-1769 (2014); (4) Fibroblast growth factor-21 (FGF21), a potent metabolic regulator, mainly expressed in liver and intestine, that for example, lowers glucose, triglycerides and low-density lipoprotein—see Molecular Metabolism, 3, 221-229 (2014); Low levels of FGF21 predict incident diabetes and can serve as a useful biomarker—see Clin. Endocrinol. 86, 37-43 (2017); a long-acting pegylated FGF21 has been reported to reduce liver fat, liver injury and fibrosis in patients with NASH (press release Bristol-Myers-Squibb, 22 Apr. 2017.

This invention emerged from the possibility that the above listed enteroendocrine hormones can be covalently modified at reactive lysine (lys) and arginine (arg) residues by electrophilic microbial metabolites produced in the intestines. Physiological benefit was hoped to result from the use of a small molecule agent which could intercept microbial electrophiles and thus preserve hormonal activity. Chemical logic led to the focus on microbial electrophiles as possible culprits, even though in principal other types of reactive microbial species could be formed in the gut—for example, nucleophiles, free radicals or oxidizing molecules—because of the importance and reactivity of lysine amino groups and arginine guanidino residues, as explained in detail below. In addition, microbes in the gut normally produce a large variety of carbonyl compounds that have sufficient reactivity to combine with arginine and lysine side-chains of neuropeptide hormones. Examples of such carbonyl compounds are fructose, acetone, pyruvate, alpha-ketoglutarate, oxaloacetate, acetoacetate and other beta keto acids formed by beta oxidation of fatty acids, formaldehyde, acetaldehyde, glyoxal, malondialdehyde, methyl glyoxal. The anti-electrophiles selected for the first study contain two nucleophilic nitrogen atoms of only moderate basicity so that a considerable fraction of the molecules exist in the required unprotonated form at pH 7-8 with a free amino group, as required for reactivity with electrophiles.

Another key feature of the invention is the focus on low molecular weight compounds of high polarity and water affinity and minimum lipophilicity so that they are not absorbed into the circulation after oral administration, but remain in the gastrointestinal tract until discharge with the feces. Less than 5% of the oral dose is absorbed into the system, preferably less than 1% of the dose is absorbed. Confinement in the gut eliminates systemic exposure while maximizing the protective action against electrophiles produced by intestinal microbes. Such very safe medicinal agents are ideally suited for prophylaxis against T2D and NASH, as well as agents for effective therapy, especially when combined with physical exercise and weight control. An example of such a molecule is the dipolar ion of formula I and its conjugate base II which are in rapid equilibrium at pH 7, the pKa of I being ca. 7.7.

The molecular system I and II, which will be referred to as I/II herein is so polar and so highly solvated by water (C log P=−3.2; calculated from Chemdraw Professional 16.0) that it cannot diffuse through lipid membranes or the intestinal walls. In general, compounds having C log P values below −1.0 are not readily absorbed, but some polar compounds (e.g. amino acids) are absorbed in relatively large amounts by active transport mechanisms in the G.I. tract (>5%) and are not part of this invention.

Molecules I/II are synthesized from 2-aminomethylbenzimidazole by sulfonation using either chlorosulfonic acid at reflux or 20% oleum at room temperature following the detailed procedure described below. The dipolar ion I is a stabile colorless solid which is water soluble up to a concentration of 0.2 molar at 23 degrees C.

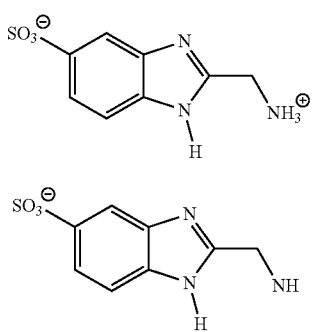

In order to test the hypothesis that a non-absorbable compound which is confined to the GI tract can favorably affect metabolic syndrome T2D and related conditions in vivo studies were carried out with I/II using a polygenic mutant strain of mice that develop metabolic syndrome, T2D and obesity when fed a high fat ("Western type") diet. This polygenic mouse model ("FATZO" mouse), developed by Eli Lilly Co. and PreClinOmics (now Crown Bio, Indianapolis, Ind.), has been described in detail (PLoS ONE, 12, 1-15 (2017). FATZO mice on a high fat diet generally gain weight, gradually become obese, and develop hyperglycemia, hypertension, glucose intolerance, insulin insensitivity and severe T2D. A group of FATZO mice were placed on a high fat diet (HFD) for an initial three-week 'base' period after which they were divided into two groups: Group 1 (the treated group) was maintained on a HFD along with 5 mg/day of I/II, administered in water by gavage. Group 2 (untreated group) received the HFD but no compound I/II. Measurements of fasting blood glucose over a further six-week period showed large differences between the two groups. Blood glucose levels of the treated group were stabile and after six weeks about 50% below those of the untreated group. In addition, the mice in the untreated group gained on average 2% of body weight per week, whereas the treated group showed no weight gain. A third group of FATZO mice was maintained on a standard diet of ordinary mouse chow and also treated with 5 mg/day of I/II. That treated group showed no weight gain and no increase in fasting blood glucose levels over the six-week period, and they showed completely normal behavior.

Analysis of the blood of mice in the treated group by HPLC/mass spectrometry demonstrated the absence of the test compound I/II—(<0.01 mg. per mouse), confirming that there is no detectable absorption of I/II from the GI tract after oral administration. These findings support the concept that gut-restricted anti-electrophilic agents such as I/II can be surprisingly effective and constitute a sound and safe therapeutic approach to the prevention and treatment of metabolic syndrome and T2D. In addition, the results demonstrate the effectiveness of the anionic sulfonate group in preventing absorption from the intestines.

In order to test further the hypothesis that intestinal peptide hormones might be compromised by the chemical action of gut microbial products, in vitro studies were carried out with GLP-1, PYY and Oxyntomodulin. For these studies methyl glyoxal was selected as electrophile because it is a well-known microbial metabolite and also relevant to metabolic syndrome, T2D and diabetic neuropathy; see Diabetes, 63, 50-52 (2014); Biochemical Soc. Transact, 42, 450-456 (2014); Clinical Sci., 128, 839-861 (2015); Hypertension, 56, 471-476 (2010). Methyl glyoxal has also been implicated in neurodegenerative diseases—see Neuroscience, 9, 1-12 (2015). Further, methyl glyoxal is formed in humans as a non-enzymic byproduct from glyceraldehyde 3-phosphate and hydroxy acetone phosphate which are essential to life. Fortunately, the body produces a pair of enzymes (glyoxalases 1 and 2; glo1 and glo2) which act in tandem to convert methyl glyoxal into R-lactic acid, which is innocuous. Glo1 and 2 are essential to life, since knockout mice without glo1 are non-viable. Methyl glyoxal can be detected in blood in amounts that correlate with the severity of T2D. Finally, methyl glyoxal is known to react with proteins, DNA and RNA and thus may contribute to various pathologies and even aging as a consequence.

The results of the in vitro studies that have been carried out using methyl glyoxal and each of three intestinal peptide hormones, GLP-1, PYY (a satiety-sensing hormone), and Oxyntomodulin, can be summarized as follows:
1. Each peptide was stirred in 0.62 mM solution in 30 mM phosphate buffer (pH 7.4) with 20 equivalents of methyl glyoxal at 37 degrees C. for 3 hours with or without compound I/II (5 equivalents relative to methyl glyoxal).

The mixture was cooled to ambient temperature and analyzed by ultra-high pressure liquid chromatography (Agilent 1290 UPLC) coupled with detection by triple time of flight mass spectrometry (Scitex 5600 TRIPTOF mass spectrometer), each aliquot being diluted with 20% aqueous acetic acid.

2. With GLP-1 as substrate (and no test compound) less than 5% unreacted GLP-1 remained, the rest being a complex mixture of products with multiple sites of modification at lysine and arginine. With GLP-1 and test compound I/II, greater than 95% of GLP-1 remained unchanged.
3. For PYY: without compound I/II, less than 1% of PYY remained, the rest being a complex mixture with multiple sites of modification at lysine and arginine. With Compound I/II, 85% of PYY remained unchanged and 15% was modified at one lysine.
4. For Oxyntomodulin: Without compound I/II, less than 1% of Oxyntomodulin remained unchanged and 99% was a complex mixture with multiple sites modified at arginine and lysine. With compound I/II, 90% of Oxyntomodulin was unchanged and 10% was converted to a product with one lysine modified.

These data provide direct evidence that electrophiles such as methyl glyoxal can damage important intestinal peptide hormone regulators. Furthermore, they provide that compound I/II can protect GLP-1, PYY, and Oxyntomodulin from damage by carbonyl-containing electrophiles produced by intestinal microbes.

The damage done by microbial electrophiles extends far beyond that inflicted on regulators in the intestines since compounds such as methyl glyoxal can easily diffuse through membranes and enter the general circulation via the portal vein and the liver. Thus, microbially produced electrophiles may cause harm throughout the body, including the organs, blood vessels, nervous system and the brain. As a specific example, it is known that methyl glyoxal induces apoptosis in pancreatic beta cells—see Nature Scientific Reports, DOI: 10.1038/srep23403 (2016). It is not unlikely that the L-cells that line the intestines, which are very important because they produce peptides hormones such as GLP-1 and PYY, might also be killed because of the toxicity of locally produced electrophiles. That in turn could result in accelerated disease progression with time. In addition, gut microbially produced circulating carbonyl electrophiles can adversely impact metabolic health by reacting with the critical catalytic arginine at the active site of AMP-activated protein kinase—the master metabolic switch (see Molecules and Medicine 56-58, as cited above).

The compound I/II is between two and three orders of magnitude more reactive toward methyl glyoxal than the guanidine subunit of arginine in derivatives such as N-tosyl-arginine methyl ester at pH 7 in aqueous solution as determined by rate studies using reverse phase HPLC analysis to follow the course of reaction as a function of time. In contrast, the standard anti-diabetic agent metformin, which is known to condense with methylglyoxal, reacts at less than one-tenth the rate as N-tosyl arginine methyl ester under the same conditions. Although the reason for the anti-diabetic activity of metformin remains uncertain, it appears not to be an efficient carbonyl scavenger—not surprising since it is a strong base (pKa 12.4) and more than 99.9% in the unreactive protonated form at pH 7.

The remarkable ability of I/II as anti-electrophilic agents acting locally in the gut to lower levels of circulating glucose is unprecedented and surprising. Because I/II do not enter the general circulation they are likely to be safe for human use and very well suited for use both therapeutically and prophylactically to prevent metabolic syndrome in conjunction with exercise and weight control. It is obvious that their successful deployment could help slow the dramatic increases in the incidence of T2D and NASH when combined with weight and dietary control. Beyond that, they might treat or protect against other conditions caused by microbial electrophiles e.g., irritable bowel syndrome.—and even protect DNA and RNA from damage by electrophiles such as methyl glyoxal. The range of human illnesses that might be prevented or ameliorated by the use of the compounds encompassed in this invention is very wide. Degenerative diseases of the brain are especially notable for several reasons, including: (1) about 20% of blood distributes to the brain which therefore is heavily exposed to microbially-produced reactive electrophiles such as methyl glyoxal that enter the circulation from the gut; (2) Parkinson's disease has been strongly linked to methyl glyoxal toxicity—see Nature Sci. Reports, 7, 12816 (2017); (3) neurons are both vulnerable and not readily replenished. Since neuronal apoptosis may also play a role in Alzheimer's disease, the compounds of the present invention may be beneficial in preventing or retarding progression of this form of dementia.

Metabolic syndrome and T2D are progressive diseases in part because they tend to trigger weight gain as a consequence of increased appetite or a diminished satiety response after eating. Since neuropeptide PYY acts to signal satiety, its inactivation by electrophiles generated by gut microbes could be a cause of the weight gain that accompanies metabolic syndrome and T2D. Thus the compounds of this invention are useful in the suppression of appetite, the prevention of weight gain, in weight control, and in protection of neuropeptides in the G.I. tract.

The compounds of this invention can be administered orally in various forms including—solid tablets of the compound or in gradual release formulations of various durations. These compounds contain a carbon attached sulfonate ion substituent which greatly increases polarity and water solubility, and decreases the likelihood of absorption into the body from the GI tract—see, J. Med. Chem., 56, 5094-5114 (2013). Simple aryl sulfonate anions, e.g. benzenesulfonate ion, are not at all absorbed and also devoid of toxicity.

There are a few other medicines that are given orally and act in the GI tract without systemic absorption to target microorganisms. These are generally non-absorbable antibiotics, an example of which is Rifaxamin whose principal use is to treat irritable bowel syndrome or traveler's diarrhea—see Clin. Infect. Diseases, 45, S77-S84 (2007); Am. J. Gastroenterol., 101, 226-233 (2006). The focus of this invention on the use of non-absorbable molecules of minimum molecular size, very high polarity and high nucleophilicity at pH 7 toward gut microbial products contrasts with a previous disclosure of the application of various polymers including polyamines as sequestering agents for dietary dicarbonyl compounds—see WO2014150873A1; EP2968403A1; US20160024233.

The new concepts of this invention suggest other classes of compounds of low molecular weight, non-absorbable, sulfonate-containing nitrogen nucleophiles (MW<800, pKa between 5 and 10, preferably pKa between 6 and 9, more preferably pKa between 7 and 8), which can serve as therapeutic agents, acting locally in the intestines to combine (via C—N bond formation) with and neutralize microbially-produced electrophilic carbonyl species in order: (1) to protect gastrointestinal peptide hormones containing arginine or lysine residues from attack, and (2) to prevent diffusion of these microbial toxins from the gut into the general circulation where they can cause systemic damage to proteins, DNA or RNA; and the application of these therapeutic agents to the prevention or treatment of metabolic syndrome, type 2 diabetes, steatohepatitis, obesity and neurodegenerative disorders; a number of these are shown below:

Imidazoles

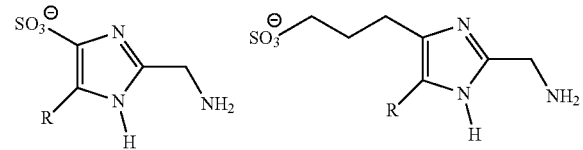

wherein R is hydrogen, CN, $C_{1-10}$ alkyl, which is linear or branched and which is unsubstituted or substituted with 1-5 halogens or phenyl, which is unsubstituted or substituted with 1-5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2CO_{1-6}$alkyl is linear or branched; phenyl which is unsubstituted or substituted with 1-5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2C_{1-6}$alkyl is linear or branched; and a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$alkyl, and $OC_{1-6}$alkyl, wherein the $C_{1-6}$alkyl and $OC_{1-6}$alkyl are linear or branched and optionally substituted with 1-5 halogens; their pharmaceutically acceptable salts, pharmaceutically acceptable N-protected derivatives, and individual stereoisomers thereof.

Heteroaromatic 1,2-diamines

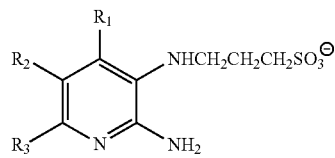

from:

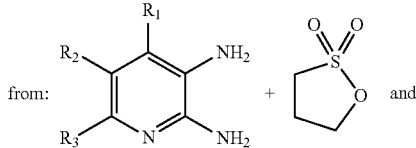 and

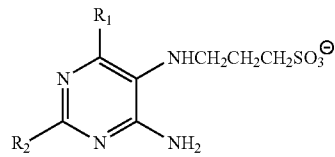

from:

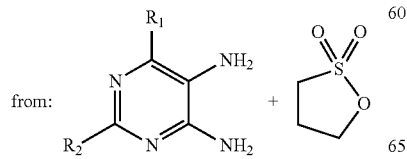

wherein $R_1$, $R_2$, $R_3$ are independently selected from the definition of R immediately above.

Azabenzamidines

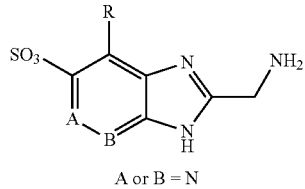

A or B = N wherein R is selected from the definition of R above.

Guanidines

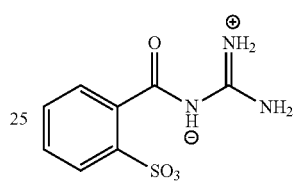

Similarly, the meta, and para isomers from acylation of guanidine from: 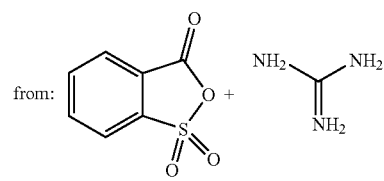

which may be substituted by one or more R groups on the aromatic ring, wherein R is independently selected from the definition of R above.

Acrylic Diamines

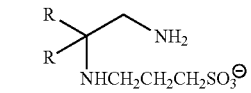

from: 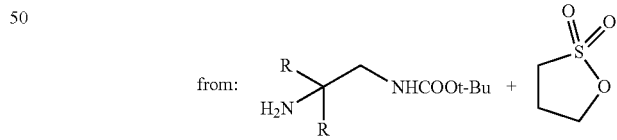

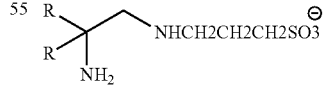

from: 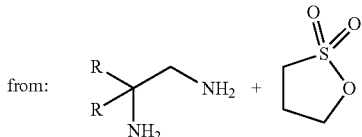

wherein R is independently selected from the definition of R above.

Benzoimidazoles:

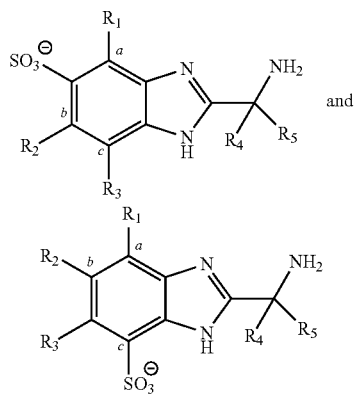

wherein $R_1$, $R_2$, and $R_3$ are independently selected from hydrogen, CN, $C_{1-10}$ alkyl which is linear or branched and which is unsubstituted or substituted with 1-5 halogens or phenyl, which phenyl is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; phenyl which is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; and a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$ alkyl, and $OC_{1-6}$ alkyl, wherein the $C_{1-6}$ alkyl and $OC_{1-6}$ alkyl are linear or branched and optionally substituted with 1-5 halogens;

$R_4$ and $R_5$ are independently selected from H, linear or branched $C_1$-$C_8$-alkyl, aryl or heteroaryl, $R^6$ are independently selected from H, linear or branched $C_{1-8}$ alkyl, aryl or heteroaryl, their pharmaceutically acceptable salts, pharmaceutically acceptable N-protected derivatives, and individual stereoisomers thereof.

In general, amines may be protected as derivatives of 1-chloroethyl carbamate (ACE), 4-methoxybenzenesulfonamide, acetamide (Ac), benzylamine (Bn), benzyloxy carbamate (CBz), formamide, methyl carbamate, trifluoroacetamide, and tert-Butoxy carbamate (Boc).

In general, amine salts of the invention may be formed with pharmaceutically acceptable acids including: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (–L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (–L), salicylic acid, sebacic acid, stearic acid, succinic acid, sulfuric acid, tartaric acid (+L), thiocyanic acid, toluenesulfonic acid (p), and undecylenic acid.

Pharmaceutically acceptable cations which may form salts of negatively charged groups within compounds of the invention include: $Na^+$, $K^+$, $Ca^{2+}$, $Mg^{2+}$, $Zn^{2+}$, and $Al^{3+}$.

Stereoisomers as defined herein are isomeric molecules that have the same molecular formula and sequence of bonded atoms, but differ in the three-dimensional orientations of their atoms in space. This contrasts with structural isomers, which share the same molecular formula, but the bond connections or their order differs. By definition, molecules that are stereoisomers of each other represent the same structural isomer.

EXAMPLES

The benzimidazole sulfonate compounds of the present invention are readily synthesized by well-known organic synthetic processes as shown in the following sections.

Scheme:

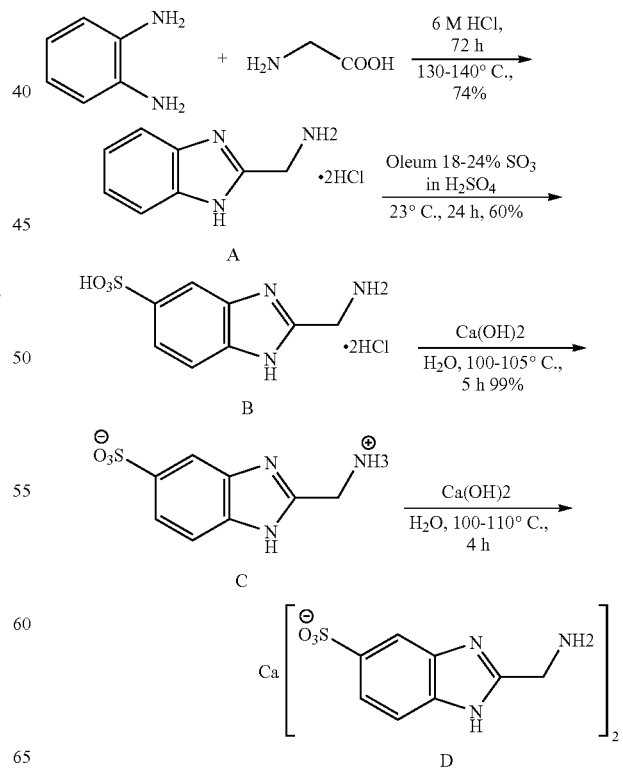

Example 1: (1H-Benzo[d]imidazol-2-yl) methanamine Dihydrochloride

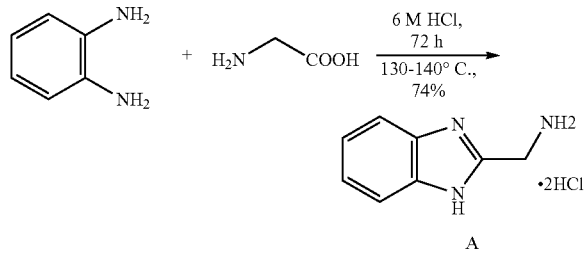

A solution of glycine (10 g, 53.1 mmol) and o-phenylenediamine (14.4 g, 53.1 mmol) in 6 M HCl (100 mL) was heated at reflux for 72 h (bath at 130-140° C.) under nitrogen. The reaction mixture was allowed to cool to room temperature, the resulting off white solid was collected by filtration and dried to give 15.8 g of solid, any color was removed by treatment with 50 wt. % charcoal in water at 100° C. Filtration through Celite and concentration under reduced pressure gave a yellow solid, which was dried by the addition of toluene and evaporation under reduced pressure to give pure (1H-benzo[d]imidazol-2-yl)methanamine dihydrochloride salt (14.5 g, 74% yield).

$^1$HNMR (DMSO-$d_6$, 400 MHz) δ 7.48-7.45 (m, 2H), 7.11-7.09 (m, 2H), 3.90 (s, 2H). See, Org. Lett. 2009, 11, 907-910.

Example 2: (5-Sulfo-1H-benzo[d]imidazol-2-yl) methanaminium hydrogen sulfate (B)

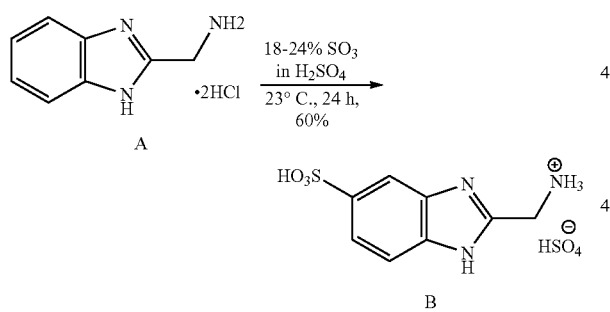

Oleum (~18-24% free $SO_3$) (20 mL) was added to the above benzimidazole dihydrochloride salt (A) (4 g, 18.2 mmol) at 0° C., and the mixture was stirred for 24 h at 23° C., the reaction mixture was poured on to crushed ice (3 g/mL of oleum). After storage at 23° C. for 12 h, a light yellow solid precipitated which was separated by filtration, dried and washed with methanol (~40 mL) to give after drying under vacuum, a free flowing solid (4.8 g).

The above product was recrystallized from hot water (5 mL/1 g of product), collected by filtration dried in vacuum to give a yellow solid compound (2.3 g, 60% yield). If an impurity was detected by $^1$HNMR analysis an additional recrystallization was performed.

$^1$HNMR ($D_2O$, 400 MHz) δ 8.01 (s, 1H), 7.82 (1H, d, J=3.2 Hz), 7.76 (1H, d, J=3.2 Hz), methelene proton signals merging with water, ESI-MS, for $C_8H_9N_3O_3S$ for: [M+1]: 228.

LC-MS/HPLC: $R_t$ 0.284 (254 nm); ACN/$H_2O$=5:95 gradient (both mobile phase has 0.1% formic acid); (MS: 228 (M+1)); Agilent (Zorbax Eclipse plus C18, column)

Example 3: 2-(Aminomethyl)-1H-benzol[d]imidazole-5-sulfonate (C)

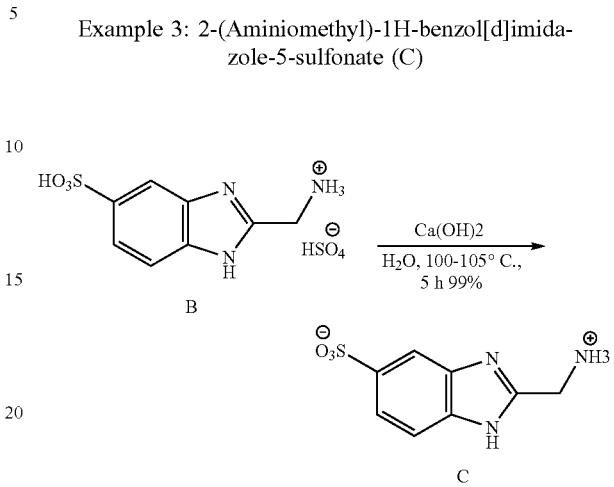

Calcium hydroxide (1.1 g, 15.47 mmol) was added to the solution of sulfate salt (B) (5 g, 15.47 mmol) in water (1000 mL) at 23° C. and the mixture was refluxed for 4 h. About 75% of the water was removed under reduced pressure, and the concentrate was stored for 3 h at 0° C., forming a solid which precipitated was removed by filtration, washed with cold water and dried to gave zwitter ionic compound (C) (3.48 g, 99%).

$^1$HNMR ($D_2O$, 400 MHz) δ 8.01 (s, 1H), 7.62-7.60 (s, 2H), 4.41 (s, 2H)

Example 4: Calcium Salt (6)

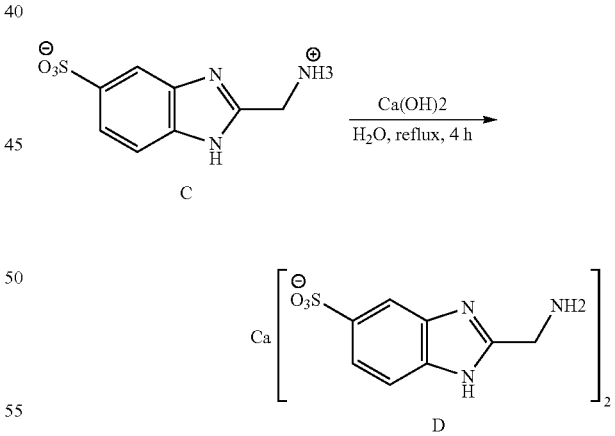

Calcium hydroxide (0.32 g, 4.40 mmol) was added to a solution of the above zwitter ionic compound (C) (1 g, 4.40 mmol) in water (800 mL) at 23° C., and the mixture was refluxed for 4 h. Water was removed under reduced pressure to give a white solid, which was separated by filtration and washed with a small amount of cold water to afford calcium salt (D) (1.25 g, 100%).

$^1$HNMR ($D_2O$, 400 MHz) δ 7.85 (s, 1H), 7.55 (1H, d, J=8.0 Hz), 7.48 (1H, d, J=8.0 Hz, 1H), 3.915 (s, 2H).

Example 5: Chlorosulfonic Acid Method (5-Sulfo-1H-benzo[d]imidazol-2-yl)methanaminium hydrogen sulfate (B)

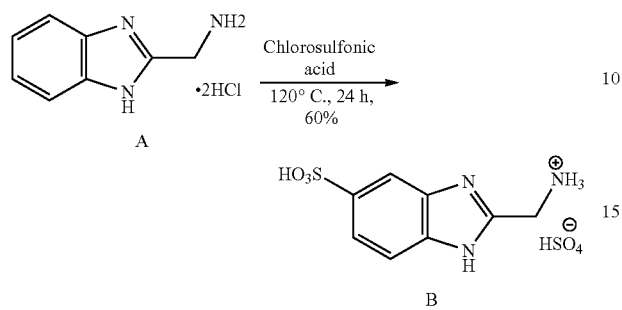

Chlorosulfonic acid (40 mL) was added to the above benzimidazole dihydrochloride salt (A) (4 g, 18.2 mmol) at 0° C., and the mixture was stirred for 24 h at 120° C. (bath at temperature) under nitrogen. About 75% of the chlorosulfonic acid was removed under reduced pressure, and the concentrate was poured on to crushed ice. After storage at 23° C. for 12 h, a light yellow solid precipitated which was separated by filtration, dried and washed with methanol (~20 mL) to give after drying under vacuum, a free flowing solid (3.8 g).

The above product was recrystallized from hot water (5 mL/1 g of product), collected by filtration following analogs of dried in vacuum to give a yellow solid compound (1.8 g, 60% yield). If an impurity was detected by $^1$HNMR analysis, an additional recrystallization performed. The spectral and analytical data were identical with product obtained from the oleum method.

Example 6: Analogs of Compound C

The following analogs of compound C above were prepared using analogous procedures starting with ortho-phenylenediamine and either S- or R-alanine or dimethylglycine:

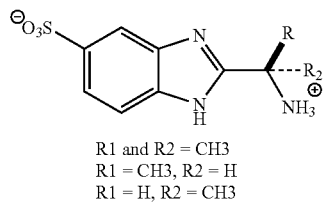

R1 and R2 = CH3
R1 = CH3, R2 = H
R1 = H, R2 = CH3

The invention claimed is:

1. An oral pharmaceutical composition which neutralizes microbially-produced electrophilic carbonyl species, comprising:
    a non-absorbable compound containing one or more nitrogen nucleophiles having a first pKa between 5 and 10, and a molecular weight less than 800,
    wherein said non-absorbable compound reacts locally in the gastrointestinal tract and combines with microbially-produced electrophilic carbonyl species by C-N bond formation, thereby protecting gastrointestinal peptide hormones containing arginine or lysine residues, and preventing diffusion of said electrophilic species into systemic circulation where they may cause damage to proteins, DNA or RNA; and
    a pharmaceutically acceptable carrier or excipient.

2. The pharmaceutical composition of claim 1, wherein said non-absorbable compound is

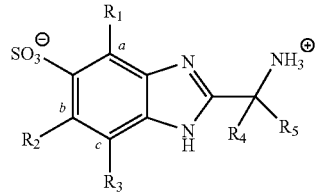

wherein $R_1$, $R_2$, and $R_3$ are independently selected from hydrogen, CN, $C_{1-10}$ alkyl which is linear or branched and which is unsubstituted or substituted with 1-5 halogens or phenyl, which phenyl is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; phenyl which is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; and a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$ alkyl, and $OC_{1-6}$alkyl, wherein the $C_{1-6}$ alkyl and $OC_{1-6}$ alkyl are linear or branched and optionally substituted with 1-5 halogens;

$R_4$ and $R_5$ are independently selected from H, linear or branched $C_1$-$C_8$-alkyl, aryl or heteroaryl, $R^6$ are independently selected from H, linear or branched $C_{1-8}$ alkyl, aryl or heteroaryl, a pharmaceutically acceptable salt, pharmaceutically acceptable N-protected derivative, or individual stereoisomer thereof.

3. The pharmaceutical composition of claim 2, wherein said non-absorbable compound is

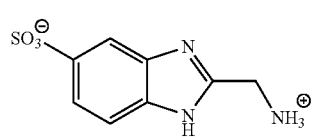

a pharmaceutically acceptable salt, pharmaceutically acceptable N-protected derivative, or individual stereoisomer thereof.

4. The pharmaceutical composition of claim 1, wherein said non-absorbable compound is selected from

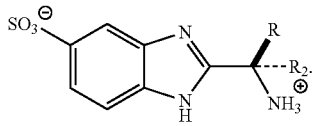

$R_1$ and $R_2 = CH_3$
$R_1 = CH_3, R_2 = H$
$R_1 = H, R_2 = CH_3$

5. The pharmaceutical composition of claim 1, wherein said non-absorbable compound is

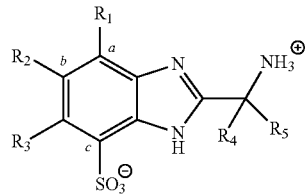

wherein $R_1$, $R_2$, and $R_3$ are independently selected from hydrogen, CN, $C_{1-10}$ alkyl which is linear or branched and which is unsubstituted or substituted with 1-5 halogens or phenyl, which phenyl is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; phenyl which is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; and a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$ alkyl, and $OC_{1-6}$ alkyl, wherein the $C_{1-6}$ alkyl and $OC_{1-6}$ alkyl are linear or branched and optionally substituted with 1-5 halogens;

$R_4$ and $R_5$ are independently selected from H, linear or branched $C_1$-$C_8$-alkyl, aryl or heteroaryl, $R^6$ are independently selected from H, linear or branched $C_{1-8}$ alkyl, aryl or heteroaryl, a pharmaceutically acceptable salt, pharmaceutically acceptable N-protected derivative, or individual stereoisomer thereof.

6. A compound of formula

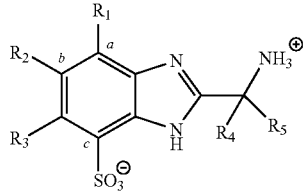

wherein $R_1$, $R_2$, and $R_3$ are independently selected from hydrogen, CN, $C_{1-10}$ alkyl which is linear or branched and which is unsubstituted or substituted with 1-5 halogens or phenyl, which phenyl is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; phenyl which is unsubstituted or substituted with 1-5 substituents independently selected from halogen, CN, OH, $R^6$, $OR^6$, $NHSO_2R^6$, $SO_2R^6$, $CO_2H$, and $CO_2C_{1-6}$ alkyl, wherein the $CO_2C_{1-6}$ alkyl is linear or branched; and a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$ alkyl, and $OC_{1-6}$ alkyl, wherein the $C_{1-6}$ alkyl and $OC_{1-6}$ alkyl are linear or branched and optionally substituted with 1-5 halogens;

$R_4$ and $R_5$ are independently selected from H, linear or branched $C_1$-$C_8$-alkyl, aryl or heteroaryl, $R^6$ are independently selected from H, linear or branched $C_{1-8}$ alkyl, aryl or heteroaryl, molecular weight <800, and a pKa between 5 and 10;

a pharmaceutically acceptable salt, pharmaceutically acceptable N-protected derivative, or individual stereoisomer thereof.

* * * * *